Figure 1:
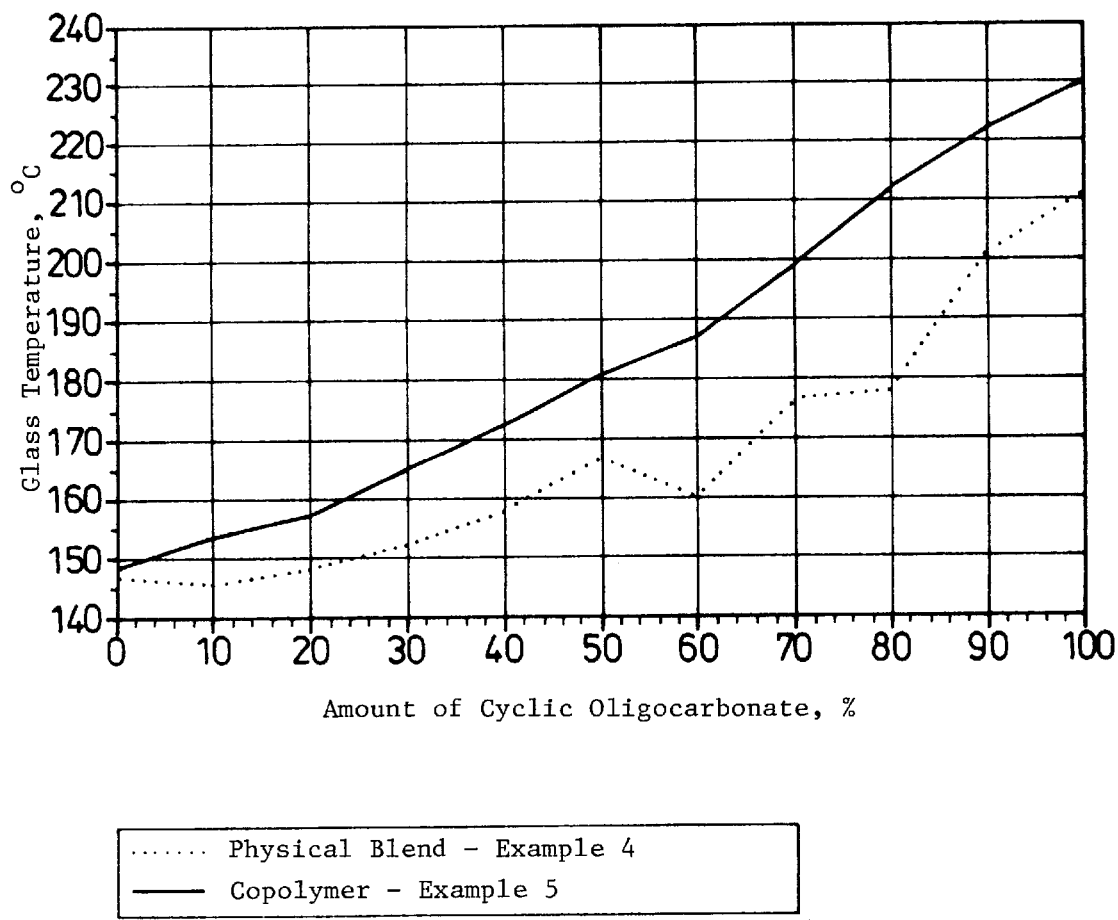

United States Patent [19]
Köhler et al.

[11] Patent Number: 6,156,871
[45] Date of Patent: Dec. 5, 2000

[54] MIXTURES OF CYCLIC OLIGOCARBONATES, THEIR PRODUCTION AND USE

[75] Inventors: Burkhard Köhler, Leverkusen; Duane Priddy, Jr., Krefeld; Yun Chen, Krefeld; Harald Pielartzik, Krefeld; Robert Kumpf, Düsseldorf, all of Germany

[73] Assignees: Bayer Aktiengesellschaft, Leverkusen, Germany; Bayer Corporation, Pittsburgh, Pa.

[21] Appl. No.: 08/923,848

[22] Filed: Sep. 4, 1997

[30] Foreign Application Priority Data

Sep. 9, 1996 [DE] Germany .................. 196 36 539

[51] Int. Cl.$^7$ .................................................. C08G 64/00
[52] U.S. Cl. ....................... 528/371; 528/372; 560/125
[58] Field of Search ..................... 528/371, 372; 560/125

[56] References Cited

U.S. PATENT DOCUMENTS

| | | | |
|---|---|---|---|
| 3,386,954 | 6/1968 | Schnell et al. | 260/47 |
| 4,605,731 | 8/1986 | Evans et al. | 528/371 |
| 4,616,077 | 10/1986 | Silva | 528/371 |
| 4,650,852 | 3/1987 | Evans et al. | 528/371 |
| 4,727,134 | 2/1988 | Brunelle et al. | 528/371 |
| 4,982,014 | 1/1991 | Freitag et al. | 568/721 |
| 5,126,428 | 6/1992 | Freitag et al. | 528/196 |
| 5,227,458 | 7/1993 | Freitag et al. | 528/196 |

FOREIGN PATENT DOCUMENTS

| | | |
|---|---|---|
| 1229101 | 11/1966 | Germany . |
| 4029808 | 3/1992 | Germany . |

OTHER PUBLICATIONS

Macromolecules (month unavailable) 1991, 24, pp. 3035–3044.
Indian Journal of Technology, vol. 31, Apr.–Jun. 1993, pp. 234–246.
J. Am. Chem. Soc. (month unavailable) 1990, 112, pp. 2399–2402.

*Primary Examiner*—Joseph McKane
*Assistant Examiner*—Joseph Murray
*Attorney, Agent, or Firm*—Joseph C. Gil; Aron Preis

[57] ABSTRACT

The present invention relates to mixtures of cyclic oligocarbonates, to their production by way of mixtures of bischloroformates, and to their use for the production of linear polycarbonates and for the modification of other linear polycarbonates.

8 Claims, 1 Drawing Sheet

....... Physical Blend – Example 4
——— Copolymer – Example 5

MIXTURES OF CYCLIC OLIGOCARBONATES, THEIR PRODUCTION AND USE

According to EP 0 359 953 (Le A 26 344), diphenols of formula (I):

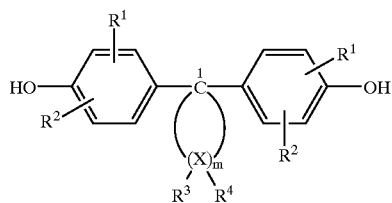

are known, in which $R^1$ and $R^2$, independently of each other, represent hydrogen, a halogen, preferably chlorine or bromine, a $C_1$–$C_8$ alkyl, a $C_5$–$C_6$ cycloalkyl, a $C_6$–$C_{10}$ aryl, preferably phenyl, and a $C_7$–$C_{12}$ aralkyl, preferably a phenyl-$C_1$–$C_4$ alkyl, particularly benzyl, m is an integer from 4 to 7, preferably 4 or 5, $R^3$ and $R^4$ represent, individually for each X, and independently of each other, hydrogen or a $C_1$–$C_6$ alkyl, and X represents carbon, with the proviso that $R^3$ and $R^4$ simultaneously represent alkyl on at least one X atom.

$R^3$ and $R^4$ preferably simultaneously represent alkyl on 1 to 2 X atoms, particularly on one X atom only.

The preferred alkyl radical is methyl; the X atoms in the α-position to the di-phenyl-substituted C atom (C-1) are preferably not dialkyl-substituted; however, alkyl substitution in the β-position to C-1 is preferred. Most preferably, an X atom is dialkyl-substituted in the β-position and an X atom is monoalkyl-substituted in the β'-position.

These known diphenols also comprise dihydroxydiphenylcycloalkanes containing 5 and 6 ring C atoms in their cycloaliphatic radical (m=4 or 5 in formula (I)), such as diphenols of formulae:

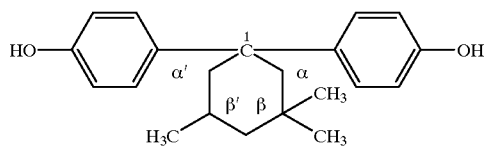

and

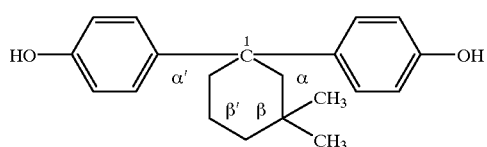

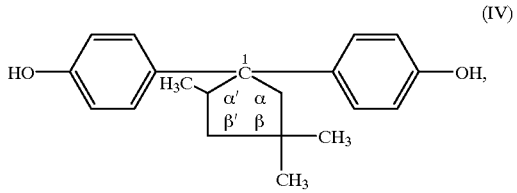

for example, where 1,1-bis(4-hydroxyphenyl)-3,3,5-trimethylcyclohexane (formula II) is particularly preferred industrially.

EP 0 359 953 also mentions mono- and bis-chloroformates of diphenols of formula (I) (page 10, lines 12–14 of this European Patent; see U.S. Pat. No. 4,982,014, column 9, lines 6 to 9, also).

Details of the preparation of these bischloroformates are not mentioned, and neither are mixtures with pre-phosgenates containing chloroformates.

It has now been shown that by employing a special preparation of the bis-chloroformates of diphenols of formula (I) they are obtained in admixture with pre-phosgenates which contain chloroformates. This preparation can be effected analogously to that described in Macromolecules 1991, 24, pages 3035–3044.

The present invention thus relates to mixtures of bischloroformates of diphenols of formula (I) with pre-phosgenates, which contain bischloroformates, of diphenols of formula (I), namely to mixtures of bischloroformates of formula (V):

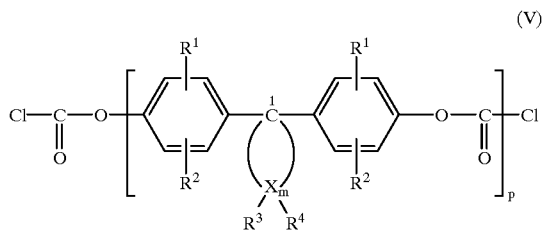

where $R^1$ to $R^4$, "m" and "X" have the meaning given for formula (I), and "p" is a number from 1 to 4 on average.

The present invention also relates to a process for producing mixtures of bischloroformates of formula (V), which is characterised in that phosgene is passed into a two-phase mixture of an organic solvent, preferably methylene chloride, with diphenols of formula (I), and water, at temperatures from –5° C. to +40° C., and a solution or suspension of an alkali metal or alkaline earth metal hydroxide is simultaneously added so that the pH is between 1 and 8, preferably between 2 and 5.

The mixtures of bischloroformates of formula (V) according to the invention are particularly suitable for the production of mixtures of cyclic aromatic oligocarbonates.

Thus the present invention also relates to the use of the mixtures of formula (V) for the production of mixtures of cyclic aromatic oligocarbonates.

The reaction of the mixtures of formula (V) to form mixtures of cyclic oligocarbonates is effected by adding a solution of (V) in an organic solvent, preferably methylene chloride, and an organic amine, preferably triethylamine, synchronously and drop-wise to a two-phase mixture of an organic solvent, preferably methylene chloride, and water, at temperatures of 0° C. to 40° C., preferably 30° C. to 40° C. A solution or suspension of an alkali metal or alkaline earth metal hydroxide is simultaneously added so that the pH is between 7 and 13, preferably between 9 and 11.

The preparation can be conducted analogously to that described in the Indian Journal of Technology 31 (1993), pages 234–246.

The mixtures of cyclic oligocarbonates exhibit various degrees of polycondensation "q", which on average are between 2 and 20.

Thus the present invention also relates to a process for producing mixtures of cyclic oligocarbonates of formula (VI):

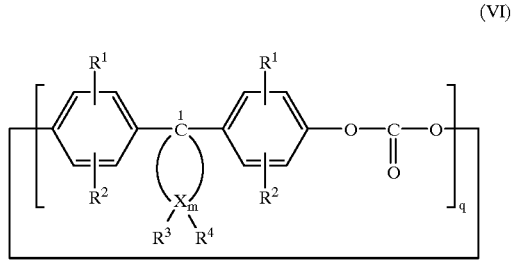

(VI)

wherein $R^1$ to $R^4$, "m" and "X" have the meaning given for formula (I), and "q" is a number from 2 to 20 on average, which is characterised in that a solution of (V) in an organic solvent, preferably methylene chloride, and an organic amine, preferably triethylamine, are added synchronously and drop-wise to a two-phase mixture of an organic solvent, preferably methylene chloride, and water, at temperatures of 0° C. to 40° C., preferably 30° C. to 40° C. A solution or suspension of an alkali metal or alkaline earth metal hydroxide is simultaneously added so that the pH is between 7 and 13, preferably between 9 and 11.

The present invention further relates to the mixtures of cyclic oligocarbonates of formula (VI) which are obtainable by the process according to the invention.

Determination of the terminal groups serves as proof that cyclic structures are present; this is effected by determining the phenolic OH terminal groups photometrically after coloration with $TiCl_4$, and by determining the nitrogen-containing terminal groups by combustion/chemiluminescence.

The oligocarbonate mixtures obtainable according to the invention have maximum terminal group contents of 0.3 mole, preferably a maximum of 0.1 mole, per mole of oligocarbonate mixture.

Cyclic oligocarbonates and the production thereof are known. (See DE-AS 1 229 101, U.S. Pat. No. 3,386,154, U.S. Pat. No. 4,727,134, J. Am. Chem. Soc. 1990, 112, pages 2399–2402, Macromolecules 1991, 24, pages 3035–3044 and Indian Journal of Technology, Vol. 31, 1993, pages 234–246, for example). These literature references do not include diphenols (I), however.

Secondly, according to EP-0 359 953 or U.S. Pat. No. 4,982,014, subsidiary amounts of cyclic oligocarbonates can be formed in conjunction during the production of polycarbonates from diphenols (I). The polycarbonate mixtures obtained according to this European Patent or US Patent have terminal group contents of at least 1.5 mole per mole of polycarbonate mixture, however.

Cyclic oligocarbonates are known according to U.S. Pat. No. 4,616,077. However, these also contain other structural units (see U.S. Pat. No. 4,616,077, column 2, line 52 et. seq.—column 3, line 10, in particular).

The mixtures of cyclic oligocarbonates of formula (VI) which are obtainable according to this invention can be converted by ring-opening polymerisation in a known manner (see for example the method according to Indian Journal of Technology 31 (1993) pages 234–246) into the high molecular weight polycarbonates of EP 0 359 953 or U.S. Pat. No. 4,982,014.

Thus the present invention also relates to the use of mixtures of cyclic oligocarbonates of formula (VI) for the production of high molecular weight polycarbonates with an $M_W$ of at least 10,000, preferably between 10,000 and 500,000 ($M_W$=weight average molecular weight, determined by gel permeation chromatography).

The present invention further relates to a process for producing high molecular weight, thermoplastic aromatic polycarbonates with an $M_W$ of at least 10,000, preferably between 10,000 and 500,000, which contain, as bifunctional structural units, only those of formula (VII):

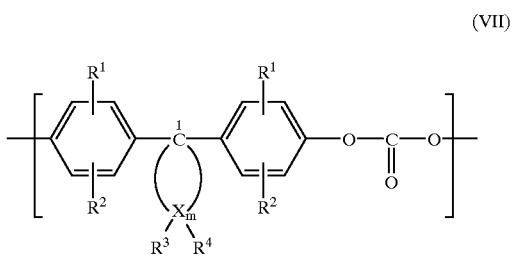

(VII)

wherein $R^1$ to $R^4$, "m" and "X" have the meaning given for formula (I), which is characterised in that cyclic oligocarbonate mixtures of formula (VI) are heated for 15 seconds to 60 minutes, preferably for 3 minutes to 30 minutes, at 200° C. to 400° C., preferably 220° C. to 350° C., in the presence of 0.001% by weight to 0.1% by weight, preferably 0.005% by weight to 0.05% by weight, with respect to the oligocarbonate mixture of formula (VI), of a catalyst.

Suitable catalysts for a ring-opening anionic polymerisation of this type are described in U.S. Pat. No. 4,650,852 and U.S. Pat. No. 4,605,731, for example. Examples of preferred catalysts include tetrabutylammonium tetraphenylborate, tetramethylammonium tetraphenylborate, lithium tetraphenylborate, tetramethylphosphonium tetraphenylborate, tetrabutylphosphonium tetraphenylborate and tetraphenylphosphonium tetraphenylborate.

The number and type of the terminal groups in a high molecular weight polycarbonate of this type are often no longer comprehensible, due to undefined secondary reactions.

One advantage of this process is that moulded parts can be obtained from high molecular weight polycarbonates such as these, which are highly viscous in the melt and which are normally no longer processable in the melt.

The mixtures of cyclic oligocarbonates of formula (VI) which are obtainable by the process according to the invention can also undergo ring-opening polymerisation in the presence of linear aromatic polycarbonates of other diphenols of formula (VIII)

HO—Z—OH          (VIII), or can be incorporated, with ring opening, in linear polycarbonates of diphenols of formula (VII), whereupon mixtures of linear polycarbonates are formed which comprise those containing structural units (VII) and those containing structural units (IX):

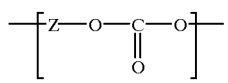
(IX)

as well as linear polycarbonates containing structural units (VII) and (IX).

The linear polycarbonates obtained from the other diphenols (VIII) which are used as co-reactants have average molecular weights $M_W$ (weight average, determined by gel permeation chromatography) of 8000 to 100,000, preferably 10,000 to 40,000, and glass transformation temperatures (determined by differential thermal analysis) of 140° C. to 180° C.

This results in certain restrictions, which are familiar to one skilled in the art, as regards the divalent aromatic radicals —Z—, which contain 6 to 30 C atoms and which may optionally also contain —O—, —S— or

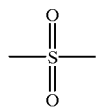

units and/or Cl or Br substituents, and thus results in certain restrictions being applicable to the diphenols (VIII) to be selected.

The preferred diphenols for the linear polycarbonates to be used as reactants are those of formula (X):

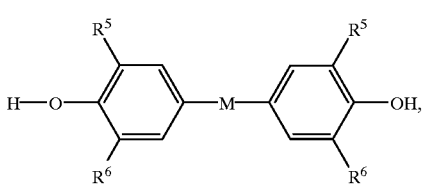
(X)

where $R^5$ and $R^6$ are the same or different and represent H, Cl, Br or $CH_3$, and —M— represents a single bond, —O—, —S—, —$SO_2$—, a $C_1$–$C_5$ alkylidene radical, a $C_2$–$C_6$ alkylene radical, a benzylidene

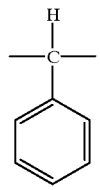

radical, a phenethylidene

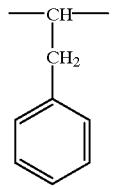

radical or an iso-phenethylidene radical

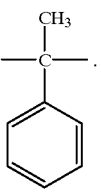

In order appropriately to adjust the molecular weights $M_W$ and glass transition temperatures of the linear polycarbonate reactants, the linear polycarbonates may also be synthesised from mixtures of other diphenols (VIII).

The ratio by weight of the cyclic oligocarbonate mixtures (VI) and the linear aromatic polycarbonate reactants obtained from other diphenols (VIII) is between 0.1% by weight to 99.9% by weight and 80% by weight to 20% by weight, and is preferably between 10 to 90% by weight and 65 to 35% by weight.

This ratio by weight of the reactants then gives rise in each case to a corresponding ratio of structural units (VII) to (IX) in the resulting mixtures of linear polycarbonates and the resulting copolycarbonates each time.

Thus the present invention also relates to the use of mixtures of cyclic oligocarbonates of formula (VI) for the modification of linear aromatic polycarbonates from other diphenols of formula (VIII) which have an $M_W$ (weight average molecular weight, determined by gel permeation chromatography) of 8000 to 100,000 and glass transition temperatures (determined by differential thermal analysis) of 140° C. to 180° C., preferably 145° C. to 152° C.

The resulting mixtures of linear polycarbonates are known from DE-OS 3 833 953 (Le A 26 397), for example; the resulting copolycarbonates are known from EP 0 359 953 referred to above and from U.S. Pat. No. 4,982,014 referred to above.

In particular, the process conditions determine whether mixtures of linear polycarbonates are predominantly formed or whether copolycarbonates are predominantly formed.

Thus the present invention also relates to a process for producing mixtures of linear polycarbonates, comprising those which contain structural units (VII) and those which contain structural units (IX), and linear copolycarbonates which contain structural units (VII) and (IX), which is characterised in that:

A) linear aromatic polycarbonates a) which contain structural units of formula (IX)

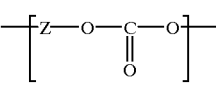
(IX)

where —Z— is a divalent aromatic radical which contains 6 to 30 C atoms and which may optionally also contain —O—, —S— or

units and/or Cl or Br substituents, b) which have weight average molecular weights $M_W$ of 8000 to 100,000, preferably 10,000 to 40,000, and d) which have glass transition temperatures of 140° C. to 180° C., preferably 145° C. to 152° C., and B) mixtures of cyclic oligocarbonates of formula (VI):

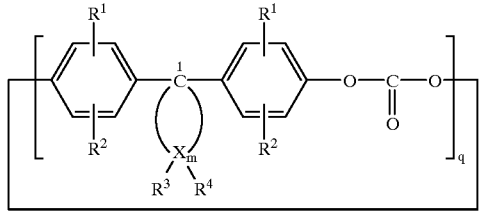

(VI)

where $R^1$ to $R^4$, "m" and "X" have the meaning given for formula (I), and "q" is a number from 2 to 20 on average, are mixed in the melt at temperatures of 200° C. to 400° C., preferably 220° C. to 350° C., in ratios by weight between 0.1% by weight of component B) to 99.9% by weight of component A) and 80% by weight of component B) to 20% by weight of component A), optionally in the presence of catalysts, for between 10 seconds and 60 minutes, preferably between 30 seconds and 3 minutes.

The mixtures of linear polycarbonates obtained have average weight average molecular weights (determined by gel permeation chromatography) of 8000 to 100,000, preferably 10,000 to 40,000. They also have a glass transition temperature which is improved compared with that of purely physical mixtures of components A)+B).

One advantage of this process is that only one variant of the linear polycarbonates has to be produced, and subsequent variation of the glass transition temperature can be effected by a mixing step.

The optional catalysts include dibutyltin oxide, cobalt(II) acetate tetrahydrate, antimony(III) oxide, manganese(II) acetate tetrahydrate, titanium(IV) butoxide, zinc acetate dihydrate, dibutyltin dilaurate, tin(II) acetate tetramethyldiacetoxystannoxane, tin(IV) oxide, lead(II) acetate trihydrate, dibutyltin diacetate, sodium benzoate and titanium(IV) bis(ethyl acetoacetate).

Examples of mixtures of bischloroformates of formula (V) include those of formula (Va):

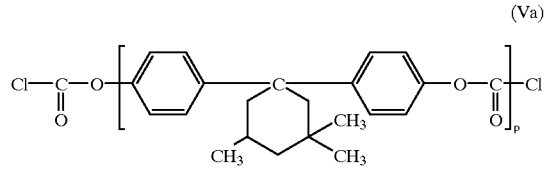

(Va)

where "p" has a value of about 1~1.3, and of formula (Vb):

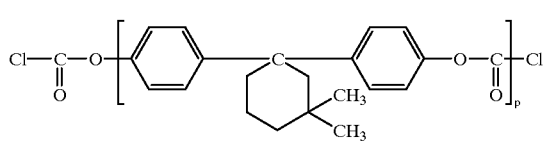

(Vb)

where "p" has a value of about 1~1.3.

Examples of mixtures of cyclic oligocarbonates of formula (VI) include those of formula (VIa):

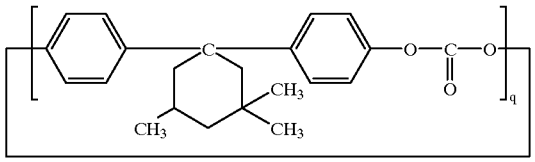

(VIa)

where "q" is 3 to 4 on average.

The mixtures of cyclic oligocarbonates of formula (VIa) contain 0.03 mole of terminal groups per mole of mixture.

Examples of suitable diphenols (VIII) include 4,4'-dihydroxydiphenyl, 2,2-bis-(4-hydroxyphenyl)-propane, 2,4-bis(4-hydroxyphenyl)-2-methylbutane, 1,1-bis-(4-hydroxyphenyl)-cyclohexane, α,α-bis-(4-hydroxyphenyl)-p-di-isopropylbenzene, 2,2-bis-(3-methyl-4-hydroxyphenyl)-propane, 2,2-bis-(3-chloro-4-hydroxyphenyl)-propane, bis-(3,5-dimethyl-4-hydroxyphenyl)-methane, 2,2-bis-(3,5-dimethyl-4-hydroxyphenyl)-propane, bis-(3,5-dimethyl-4-hydroxyphenyl)-sulphone, 2,4-bis-(3,5-dimethyl-4-hydroxyphenyl)-2-methylbutane, 1,1-bis-(3,5-dimethyl-4-hydroxyphenyl)-cyclohexane, α,α-bis-(3,5-dimethyl-4-hydroxy-phenyl)-p-diisopropylbenzene, 2,2-bis-(3,5-dichloro-4-hydroxyphenyl)-propane, 2,2-bis-(3,5-dibromo-4-hydroxyphenyl)-propane and 2,2-bis-(3-allyl-4-hydroxyphenyl)-propane.

Examples of preferred diphenols (VIII) include 2,2-bis-(4-hydroxyphenyl)-propane, 2,2-bis-(3,5-dimethyl-4-hydroxyphenyl)-propane, 2,2-bis-(3,5-dichloro-4-hydroxyphenyl)-propane, 2,2-bis-(3,5-dibromo-4-hydroxyphenyl)-propane, 1,1-bis-(4-hydroxy-phenyl)-cyclohexane and 2,2-bis-(3-allyl-4-hydroxyphenyl)-propane.

In the two processes according to the invention for the further processing of the mixtures of cyclic oligocarbonates of formula (VI) according to the invention, the additives which are customary for polycarbonates, such as demoulding agents, stabilisers against heat and UV light, flame retardants, etc., can be added in the usual amounts whilst the process is being carried out. (See EP 0 359 953, page 12, line 20 et. seq. and DE-OS 38 33 953, page 13, line 54 et. seq., for example, for further details).

Both the processes according to the invention for the further processing of oligocarbonate mixtures can directly adjoin the production of any desired moulded parts. This is effected as follows: during the ring-opening polymerisation of oligocarbonate mixtures, moulding is effected directly during polymerisation (reaction moulding). Polycarbonate mixtures obtained from cyclic oligocarbonates and linear polycarbonates are subsequently moulded as usual by injection moulding or extrusion.

The polycarbonate moulded parts obtained can be used or consumed industrially in the known manner (see EP 0 359 953 again, page 12, line 31 et. seq. and DE-OS 38 33 953, page 13, lines 67–68 and page 14, lines 1 and 2), for example in the automobile field and in the electrical field.

EXAMPLES

Example 1

Preparation of a mixture of bischloroformates of formula (Va) analogously to Macro-molecules 1991, 24, pages 3035–3044.

300 g phosgene was passed at 0° C., over a period of 150 minutes, into a mixture of 310 g (1 mole) bisphenol (II), 80 ml $H_2O$ and 1.2 liters $CH_2Cl_2$. A 25% by weight aqueous solution of sodium hydroxide was added simultaneously, so that the pH of the mixture was between 2 and 5. About 1 liter of sodium hydroxide solution was required for this purpose. After passing in phosgene, the pH was adjusted to 8–9 and nitrogen was passed in until the solution was free from phosgene. After phase separation, the organic phase was washed with 1 N HCl and then with water, dried over sodium sulphate and concentrated. The yield was 327 g. The content of hydrolysable chlorine was 13.4%, compared with a value of 16.3% for the pure bischloroformate of diphenol (II). This gave a value of "p" of 1.28.

Example 2

Preparation of a mixture of cyclic oligocarbonates of formula (VIa) analogously to Indian Journal of Technology, 31 (1993), pages 234–246.

200 ml $CH_2Cl_2$, 7 ml $H_2O$, 3 ml of 9.75 molar NaOH in $H_2O$ and 2.4 ml triethylamine were placed in a 1 liter flask and a solution of 87 g of the mixture of bischloroformates of Example 1 in $CH_2Cl_2$, 59 ml of 0.75 molar NaOH in $H_2O$ and 25 ml of a 10% by weight solution of triethylamine in methylene chloride were metered in synchronously, with vigorous stirring, over 28 minutes. Metered addition of the bischloroformate solution was effected below the liquid level, by means of a peristaltic pump. After phase separation, the product was washed with 1 N HCl and then three times with water, and the organic phase was concentrated. A material was obtained in almost quantitative yield, at least 85% of which consisted of cyclene (determination by HPLC (high performance liquid chromatography)). Further purification could be effected by re-precipitation from acetone.

$M_n$ (number average molecular weight) 1440, $M_W$ (weight average molecular weight) 2350. Both determined by gel permeation chromatography.

The glass transition temperature was 211° C. to 213° C. (amorphous mixture), as measured by differential thermal analysis.

One mole of the oligocarbonate mixture which was obtained contained 0.03 mole of terminal groups.

The phenolic OH terminal groups were determined photometrically after coloration with $TiCl_4$, and the nitrogen-containing terminal groups were determined by combustion/chemiluminescence.

Example 3

Ring-opening polymerisation:

10 g of the oligocarbonate of Example 2 was heated under nitrogen with 100 ppm tetraamnonium tetraphenylborate for 15 minutes at 340° C.

A polycarbonate was obtained which had a relative solution viscosity of 1.35 (0.5% in methylene chloride at 20° C.) and a glass transition temperature of 238° C.

Example 4 (comparison)

Blends were prepared of a linear homopolycarbonate of 2,2-bis-(4-hydroxyphenyl)-propane (relative solution viscosity 1.26, measured in $CH_2Cl_2$ at 20° C. and at a concentration of 0.5 g/100 ml; $M_W$=27,100, $M_n$=13,500, measured by gel permeation chromatography; glass transition temperature 147.3° C.) and the oligocarbonate mixture of Example 2, in various proportions by weight (0%, 10%, 20%, . . . 100%) in methylene chloride as a solvent.

Films of the solution blends were dried at 120° C. and the glass transition temperatures were determined by differential thermal analysis; they are plotted in FIG. 1 against the proportion by weight of the oligocarbonate mixture.

Example 5

Blends were prepared of a linear homopolycarbonate of 2,2-bis-(4-hydroxyphenyl)-propane (specification as in Example 4 above) and the oligocarbonate mixture of Example 2, in various proportions by weight (0%, 10%, 20%, . . . 100%), for 10 minutes in a Haake kneader at 200 revolutions/minute, at 300° C. and under nitrogen, in the presence of 150 ppm dibutyltin oxide. The glass transition temperatures were measured by different thermal analysis and are plotted in FIG. 1 against the proportion by weight of the oligocarbonate mixture.

FIG. 1 shows that the mixtures produced by reaction (Example 5) had higher glass transition temperatures than the physical blends in Example 4, which had the same original compositions.

What is claimed is:

1. Mixtures of bischloroformate of formula (V):

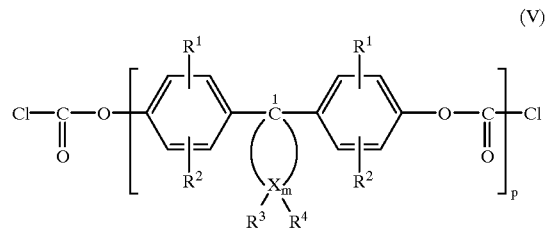

wherein $R^1$ and $R^2$, independently of each other, represent hydrogen, a halogen, a $C_1$–$C_8$ alkyl, a $C_5$–$C_6$ cycloalkyl, a $C_6$–$C_{10}$ aryl, and a $C_7$–$C_{12}$ aralkyl, m is an integer from 4 to 7, $R^3$ and $R^4$ represent, individually for each X, and independently of each other, hydrogen or a $C_1$–$C_6$ alkyl, and X represents carbon, with the proviso that $R^3$ and $R^4$ simultaneously represent alkyl on at least one X atom, and wherein "p" is a number from 2 to 4 on average.

2. A process for producing the mixtures of bischloroformates of claim 1, characterised in that phosgene is passed at temperatures of −5° C. to +40° C. into a two-phase mixture of an organic solvent with diphenols of formula (I):

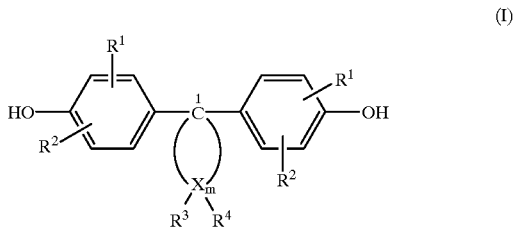

wherein $R^1$ and $R^2$, independently of each other, represent hydrogen, a halogen, a $C_1$–$C_8$ alkyl, a $C_5$–$C_6$ cycloalkyl, a $C_6$–$C_{10}$ aryl, and a $C_7$–$C_{12}$ aralkyl, m is an integer from 4 to 7, $R^3$ and $R^4$ represent, individually for each X, and independently of each other, hydrogen or a $C_1$–$C_6$ alkyl, and X represents carbon, with the proviso that $R^3$ and $R^4$ simultaneously represent alkyl on at least one X atom, and water, and a solution or suspension of an alkali metal or alkaline earth metal hydroxide is simultaneously added so that the pH is between 1 and 8.

3. The method of use of the mixtures of bischloroformates of claim 1 for the production of cyclic aromatic oligocarbonates comprising adding synchronously and drop-wise a solution of said bischloroformates and an organic amine in an organic solvent to a two phase mixture of an organic solvent and water wherein pH is maintained between 7 and 13 by the simultaneous addition of a solution or suspension of alkali metal hydroxide or alkaline earth metal hydroxide.

4. A process for producing mixtures of cyclic oligocarbonates of formula (VI):

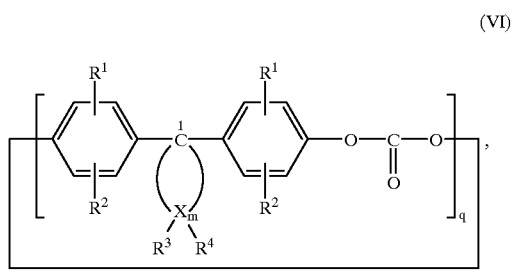
(VI)

wherein $R^1$ to $R^4$, "m" and "X" have the meaning given for formula (V) in claim 1, and "q" is a number from 2 to 20 on average, characterised in that a solution of the mixtures of bischloroformates of formula (V) in an organic solvent, and an organic amine, are added synchronously and drop-wise to a two-phase mixture of an organic solvent and water at temperatures of 0° C. to 40° C. while a solution or suspension of an alkali metal or alkaline earth metal hydroxide is simultaneously added so that the pH is between 7 and 13.

5. Mixtures of cyclic oligocarbonates of formula (VI) produced by the method of claim 4.

6. The method of use of cyclic oligocarbonates of formula (VI) of claim 5 for the production of high molecular weight polycarbonate with an $M_W$ of at least 10,000 comprising heating said cyclic oligocarbonates for 15 seconds to 60 minutes at 200 to 400° C. in the presence of 0.001 to 0.1 percent of a catalyst, said percent being relative to the weight of said oligocarbonates.

7. A process for the production of high molecular weight thermoplastic aromatic polycarbonates with a $M_W$ of at least 10,000 which contain, as bifunctional structural units, only those of formula (VII):

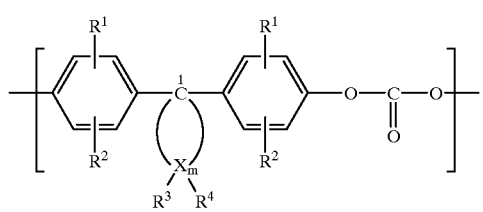
(VII)

wherein $R^1$ to $R^4$, "m" and "X" have the meaning given for formula (V) in claim 1, characterised in that cyclic oligocarbonate mixtures of formula (VI) of claim 5 are heated for 15 seconds to 60 minutes at 200° C. to 400° C., in the presence of 0.001% by weight to 0.1% by weight, with respect to the oligocarbonate mixture of formula (VI), of a catalyst.

8. A process for producing mixtures of linear polycarbonates from those which contain structural units (VII) of claim 7 and those which contain structural units (IX), and linear copolycarbonates which contain structural units (VII) and (IX), characterised in that:

A) linear aromatic polycarbonates
  a) which contain structural units of formula (IX)

(IX)

where —Z— is a divalent aromatic radical which contains 6 to 30 C atoms and which may optionally also contain —O—, —S— or

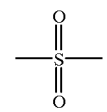

units and/or Cl or Br substituents,
  b) which have weight average molecular weights $M_W$ of 8000 to 100,000, and
  d) which have glass transition temperatures of 140° C. to 180° C., and B) mixtures of cyclic oligocarbonates of formula (VI):

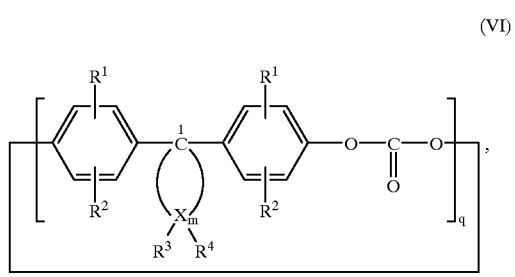
(VI)

wherein $R^1$ to $R^4$, "m" and "X" have the meaning given for formula (V) in claim 1, and "q" is a number from 2 to 20 on average, are mixed in the melt at temperatures of 200° C. to 400° C., in ratios by weight between 0.1% by weight of component B) to 99.9% by weight of component A), optionally in the presence of catalysts, for between 10 seconds and 60 minutes.

* * * * *